United States Patent [19]

Swim et al.

[11] Plant 5,077

[45] Aug. 2, 1983

[54] HYBRID TEA ROSE PLANT CV. SOUTHERN BELLE

[75] Inventors: Herbert C. Swim, Ontario; Arnold W. Ellis, Garden Grove, both of Calif.

[73] Assignee: Armstrong Nurseries, Inc., Ontario, Calif.

[21] Appl. No.: 351,113

[22] Filed: Feb. 22, 1982

[51] Int. Cl.[3] ..... A01H 5/00

[52] U.S. Cl. ..... Plt./12

[58] Field of Search ..... Plt./11-12

*Primary Examiner*—Robert E. Bagwill

*Attorney, Agent, or Firm*—Synnestvedt & Lechner

[57] ABSTRACT

A hybrid tea rose plant having two-toned blossoms of pink with a white reverse.

1 Drawing Figure

This invention relates to a new class of hybrid tea rose cv. Southern Belle. The plant is a half-hardy outdoor seedling of the bush type, cultivated for garden decoration. It was propagated by Herbert C. Swim and Arnold W. Ellis in Ontario, Calif., having as its seed parent "Pink Parfait", U.S. Plant Pat. No. 1,904, and, as its pollen parent, "Phoenix", U.S. Plant Pat. No. 3,438.

The new rose plant cv. Southern Belle is particularly characterized by the following combination of characteristics: its bright two-toned pink and white coloration is very uniform throughout the life of the flower; its large (4 to 5 inch) well-formed flowers are generally borne in clusters giving an abundant, nearly continuous bloom throughout the growing season; its inability to set hips—this leads to lower maintenance in the garden and assures faster rebloom; its above average disease resistance in the Ontario, Calif. locale and its abundant large foliage all contribute to the overall attractiveness of the new rose. It holds its distinguishing characteristics through succeeding propagations by budding.

The new variety bears its flowers singly, usually three to five or more flowers per stem and in regular, flat clusters on strong, medium-length to long stems. Outdoors, the plant blooms almost continuously and in abundant quantities during the growing season. It has a slight tea fragrance.

This new cultivar may be distinguished from its seed parent, Pink Parfait, by the following combination of characteristics:

Southern Belle bears flowers of a two-toned pink and white coloration as described and illustrated, whereas seed parent (Pink Parfait) bears lighter pink flowers without the white reverse.

The seed parent, Pink Parfait, bears flowers that are $3\frac{1}{2}$ to $4\frac{1}{2}$ inch in diameter whereas the flowers of the new cultivar (Southern Belle) are significantly larger, of 4 to 5 inch diameter.

The new rose Southern Belle does not normally set hips as grown in Ontario, Calif., whereas the seed parent (Pink Parfait) readily sets hips bearing numerous seeds.

This new cultivar rose (Southern Belle) may be distinguished from its pollen parent (Phoenix) by the following combination of characteristics:

Phoenix bears flowers of a relatively uniform deep pink coloration, whereas the new rose bears flowers of two-toned pink and white coloration essentially as described and illustrated herein.

Whereas the new rose usually bears flowers in clusters, Phoenix generally produces only one flower per stem.

The new rose produces flowers with only one to five petaloids, whereas Phoenix bears flowers with significantly more petaloids, from 5 to 12.

Whereas Phoenix bears flowers with 36 to 40 petals, the new rose bears flowers of substantially lower petalage, 27 to 34.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon The R.H.S. Colour Chart of The Royal Horticultural Society in London, England.

BUD

The peduncle is average length to long, and average caliper, erect and stiff. It is moderately smooth with some stipitate glands and near Yellow-Green 147A.

Before the calyx breaks, the bud is medium in size, and long, pointed and ovoid in form, with foliaceous appendages and a few stipitate glands on the surface of the bud. There are usually slender foliaceous parts extending beyond the tip of the bud equal to one-half or more of its length.

As the calyx breaks, the color is between Red 53C and Red 53D.

The inner surface of the sepals has a fine, wooly tomentum; margins are lined with stipitate glands.

As the first petal opens, the bud is average in size and long, pointed and ovoid in form. The color on the outside of the basal attachment point is near Yellow-Green 154C and quickly suffuses to near Yellow-White 158D; areas exposed to sunlight blush to between Red-Purple 66C and Red 53C. The inside surface of the basal attachment zone from about $\frac{1}{4}$ to $\frac{1}{2}$ inch is near Yellow-Green 145D and changes abruptly to between Red-Purple 57C and Red 53C. The bud opens up well and is not retarded or prevented from opening by hot, wet or dry weather.

BLOOM

The size of the bloom when fully open is average to large, ranging from 4 to 5 inches. The petalage is double, with from 27 to 34 petals and from 1 to 5 petaloids, arranged regularly. The bloom is very high centered at first, becoming cupped. At first the petals remain tightly cupped, with tips reflexed outward, becoming later at maturity loosely cupped with tips reflexed outward.

The petals are of medium thickness and with the inside slightly velvety and the outside slightly shiny to satiny. The outside petals are round to broadly obovate, with a flat apex and occasionally with one notch. The intermediate petals are round and the inside petals broadly obovate with a rounded apex and occasionally with one notch. The inside petals are obovate and have a rounded apex. The colors may be modified by being bordered or margined or blotched, shaded and/or washed or tinted with other colors.

The paragraphs immediately following describe the color values observed in a flower newly opened in the month of August. The plant had been grown outdoors in Ontario, Calif.

The outer surface of the basal attachment point is near Yellow-Green 154C and quickly suffuses to between White 155A and Yellow-White 158D. Areas exposed to sunlight blush to between Red-Purple 66C and Red 53C. The inner surface of the basal attachment zone for about ¼ to ½ inch is near Yellow 2C and changes abruptly to between Red-Purple 57C and Red 53C; areas exposed to sunlight blush to between Red-Purple 61C and Red 53B.

The outer and inner surfaces of the intermediate petals were the same as the outer and inner surfaces described above but with less blushing without. The outer and inner surfaces of the inner petals was as described above but without any blushing.

The paragraph immediately following describes color values observed in a bloom which had been open for three days, outdoors, in the month of August. The plant had been grown outdoors in Ontario, Calif.

The outer surface of the basal attachment point of outside petals was near Green-White 157D and quickly suffuses to between White 155B and Yellow-White 158D; areas exposed to sunlight blush to between Red-Purple 66D and Red 53C. The inner surface of the basal attachment zone for ¼ to ½ inch is near Yellow 2D and suffuses to between Red-Purple 57D and Red 53D; areas exposed to sunlight blush to between Red-Purple 61C and Red 53B. The outer surfaces of the inside petals are as described above for the outside petals but with less blushing. The inside surfaces of the inside petals are as described for the outside petals.

The general color effect of the newly opened flower is between Red-Purple 57C and Red 53C with an off-white zone near Yellow 2C in the very center. The bloom after being three days open gives a general color effect which is between Red-Purple 61C and Red 53B with a less discernable off-white zone near White 155B in the very center. The petals drop off cleanly and are not particularly affected by cold, hot, wet or dry weather.

In August, roses grown in the garden last on the bush from 3 to 5 days. Cut roses grown outdoors and kept at living-room temperatures will last from 3 to 6 days in the month of August.

REPRODUCTIVE ORGANS

An average number of stamens are arranged regularly about the pistils.

The filaments are of a medium to long length. Most are with anthers.

The anthers are of medium size, all opening approximately at once; when moist, their color is near Yellow-Orange 15A and when dry, their color is near Greyed-Orange 164A.

Pollen is moderate in quantity and near Yellow-Orange 15B in color.

There are an average number of pistils (approximately 65 in number).

The styles are moderately uneven, average in length and caliper and loosely bunched.

The stigma is near Yellow 2D in color.

Most of the ovaries are in the calyx, but some protrude therefrom.

This variety as grown in Ontario, Calif., did not normally set hips.

FOLIAGE

The compound leaves are borne usually abundantly and usually comprise from three to seven leaflets. The leaves are of a medium size, moderately heavy and semi-glossy. The leaflets are oval in shape and have an apex and a round acuminate base. The margin is doubly serrate.

The mature foliage displays upon its upper surface a color which is between Yellow-Green 147A and Green 136A. The under surface is near Yellow-Green 148B.

The young foliage on its upper surface is between Greyed-Purple 183B and Greyed-Purple 187A in color. On its under surface, it is near Greyed-Purple 187A.

The rachis is of average size, grooved on its upper side, with a few stipitate glands; the under side is prickly with stipitate glands.

The stipules are moderately long, narrow to medium-width, with medium length points, turning out at an angle of less than 45° and are recurved toward the stem.

The plant displays a more than average resistance to mildew and blackspot compared to other commercial varieties grown under comparable conditions in Ontario, Calif.

GROWTH

The plant is of upright to spreading bush habit and much branched. It displays a very vigorous growth. The canes are of medium to heavy caliper.

The main stems are near Yellow-Green 146C in color. They bear several large prickles which are of medium to long length, hooked downwardly with medium-length, moderately broad base. The color is near Greyed-Orange 166B. There are no small prickles and no hairs.

The branches are of a color between Yellow-Green 146A and Green 139A and have thorns near Yellow-Green 146B. They bear few large prickles, which are of medium to long length, hooked downwardly with medium-length, moderately broad base. There are no small prickles and no hairs.

New shoots are near Yellow-Green 144B shaded by near Greyed-Purple 187B in color. They bear few large prickles, which are medium to long in length, hooked downwardly and having a medium-length, moderately broad base and their color is near Greyed-Purple 187B. There are no small prickles and no hairs.

We claim:

1. A new and distinct variety of rose plant of the hybrid tea class, substantially as herein shown and described, being particularly characterized in that its bright two-toned pink and white coloration is very uniform throughout the life of the flower; its large, well-formed flowers are generally borne in clusters giving an abundant, nearly continuous bloom throughout the growing season, its inability to set hips, its above average resistance to disease and its abundant large foliage.

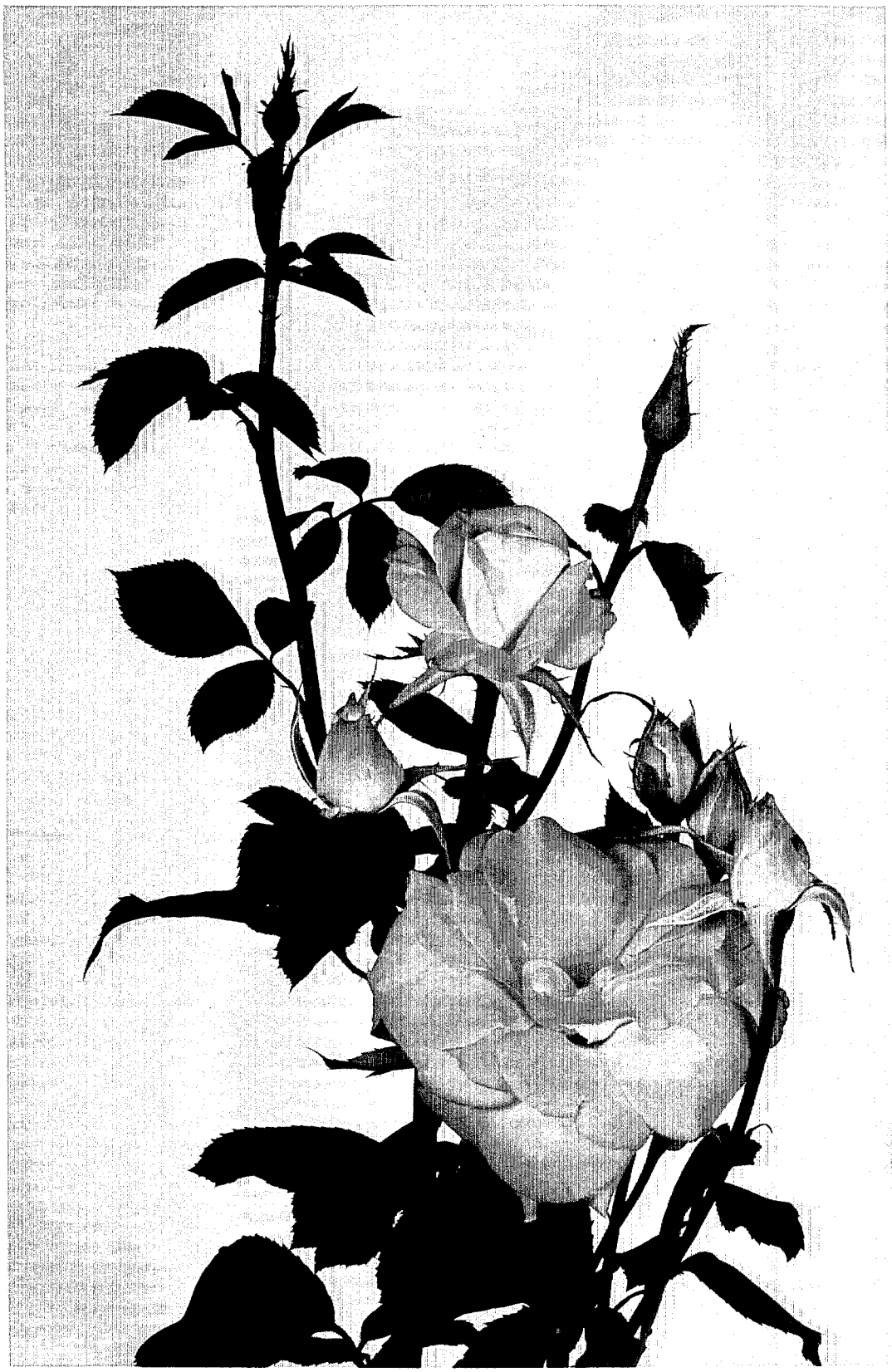

* * * * *